United States Patent [19]

Matsunaga et al.

[11] Patent Number: 5,300,128
[45] Date of Patent: Apr. 5, 1994

[54] METHOD OF PLANT TISSUE CULTURE

[75] Inventors: Tadashi Matsunaga, 2-304 Fuchu-Daisan-Jutaku, 2-41-13, Saiwai-cho, Fuchu-shi, Tokyo 183; Hitoshi Wake, Koshigaya; Mayumi Ono, Matsudo; Kiyoshi Hishinuma, Yashio; Hironori Umetsu, Tokorozawa, all of Japan

[73] Assignees: Pentel Kabushiki Kaisha; Tadashi Matsunaga, both of Tokyo, Japan

[21] Appl. No.: 22,124

[22] Filed: Feb. 25, 1993

Related U.S. Application Data

[62] Division of Ser. No. 908,894, Jul. 8, 1992, Pat. No. 5,217,892.

[30] Foreign Application Priority Data

Jul. 27, 1988 [JP] Japan .................................. 63-187889
Jul. 30, 1988 [JP] Japan .................................. 63-191284
Jul. 30, 1988 [JP] Japan .................................. 63-191285

[51] Int. Cl.$^5$ .......................... C10L 1/08; C10L 1/10
[52] U.S. Cl. ................................................... 47/57.6
[58] Field of Search ............ 47/57.605, 57.612, 57.615

[56] References Cited

U.S. PATENT DOCUMENTS

| | | | |
|---|---|---|---|
| 3,955,317 | 5/1976 | Gudin | 47/1.2 |
| 4,431,738 | 2/1984 | Maeda et al. | 435/240.54 |
| 4,562,663 | 1/1986 | Redenbaugh | 47/58 |
| 4,583,320 | 4/1986 | Redenbaugh | 47/57.6 |
| 5,217,892 | 6/1993 | Matsunaga et al. | 435/240.4 |

FOREIGN PATENT DOCUMENTS

| | | |
|---|---|---|
| 0107141 | 5/1984 | European Pat. Off. |
| 0141373 | 5/1985 | European Pat. Off. |
| 50-105881 | 8/1975 | Japan |
| 59-102308 | 6/1984 | Japan |
| 62-179384 | 8/1987 | Japan |
| 88-02399 | 4/1988 | World Int. Prop. O. |

OTHER PUBLICATIONS

Stanek et al. 1983. Folia Microbiol. 28: 91-99.
Biosis Abstract No. 81088320, Izv Akad Nauk SSSR Ser Biol., vol. 0, No. 5(1985).
Korzhenevskaya et al., Fiziologiya Rastemi, 32 (1), 1985 pp. 88-96.
Gorelova et al, Chemical Abstracts 104:48786d (1986).

Primary Examiner—David T. Fox
Assistant Examiner—Elizabeth C. Kemmerer
Attorney, Agent, or Firm—Wenderoth, Lind & Ponack

[57] ABSTRACT

A method of plant tissue culture which comprises culturing a tissue or an organ of a plant, a part of the same or cultured cells in a medium containing a culture filtrate and/or an extract of a photosynthetic procaryotic microorganism.

Such a culturing method effectively proliferates the plant tissues and cultured cells, and also promotes the formation of adventive embryos, regeneration of the plant body and production of useful substances formed by that plant.

Strains of cyanobacteria or photosynthetic bacteria are preferably used as the photosynthetic procaryotic microorganism.

15 Claims, No Drawings

METHOD OF PLANT TISSUE CULTURE

This application is a division of Ser. No. 07/908,894 filed Jul. 8, 1991, now issued as U.S. Pat. No. 5,217,892.

TECHNICAL FIELD

This invention relates to a method of plant tissue culture. More particularly, it relates to an improved method of plant tissue culture which comprises culturing a tissue or an organ of a plant, a part of the same or cultured cells to proliferate the tissue, organ or cultured cells, thereby regenerating a plant body or producing a useful substance formed by that plant.

BACKGROUND ART

In culturing plant tissue, in general, a tissue or an organ of a plant, a part of the same or cultured cells are cultivated by the use of a medium containing a plant hormone (such as auxin, cytokinin, gibberellin, ethylene and the like) in addition to nutrients essential to the growth of plants (such as inorganic salts, vitamins, sugars and the like) to form calluses, which are then cultured for several generations, thereby producing a useful substance or regenerating the original plant body therefrom.

Methods of regenerating a plant body by plant tissue culture technology may be classified into two types, i.e., differentiation and dedifferentiation, according to the kind of starting material used. The method of dedifferentiation regenerates a plant body through the dedifferentiated state of calluses or liquid-cultured cells. Typical examples include the method of developing many shoots from cluster calluses and developing roots from each shoot, thus regenerating a juvenile plant body, and the method of directly forming adventive embryos (somatic embryos) in cells, thus regenerating a juvenile plant body. When a plant body is regenerated through adventive embryos, it is known that the embryos grow to globular, heart-shaped, torpedo-shaped and mature embryos, in that order. On the other hand, the methods of differentiation employ, as the starting material, shoot apexes, dormant buds, lateral buds, embryos and seeds containing growing points, as well as hypocotyls, cotyledons and stems which contain no growing point. A typical example is the method comprising developing multiple shoots from the above-mentioned plant tissues, cutting off these multiple shoots, developing multiple shoots from each single shoot thus obtained, and finally developing roots from each of the cut shoots, thus regenerating a juvenile plant body.

In plant body regeneration by dedifferentiation cell cultivation for several generations over a long period tends to lower the ability of differentiation, resulting in a decreased rate of forming adventive embryos from cultured cells and of forming shoots and roots from calluses. When adventive embryos are artificially derived, it is common practice to investigate the type, concentration and combination of plant hormones (such as auxin and cytokinin) to be added to the culture medium, to say nothing of inorganic salt composition. However, there are many kinds of plants in which formation of adventive embryos and formation of shoots and roots from calluses cannot be expected from mere treatment with auxin or cytokinin. Adventive embryos, in particular, tend to stop growing at the stage of torpedo shape, significantly reducing the rate of redifferentiation to the plant body. Also in plant body regeneration by differentiation, studies have been made on the type, concentration and combination of plant hormones (such as auxin and cytokinin), inorganic salts and trace organic components to be added to the culture medium, but cases are known in which no formation of shoots and roots is observed, depending on the kind of plant and tissue. In both differentiation and dedifferentiation, the use of plant hormones inhibits the growth and differentiation in some cases, depending on the kind and added amount of the hormone. Hence, there has been a demand for an improved method which will enhance the rate of forming adventive embryos from various plant tissues, organs or cultured cells and which will effectively accelerate the growth of adventive embryos and the regeneration of a plant body.

Natural organic compounds produced by plants, such as alkaloids, terpenoids and various pigments, have long been used extensively as medicines and foods. For obtaining these useful substances, extraction from naturally grown or cultivated plants has long been adopted, but this is not an effective method to obtain a large quantity of the useful substances, because the mass and nature of plants are greatly influenced by natural conditions and much labor and time are needed for harvesting of plants. In recent years, planned and stable production of these useful substances is carried out by mass-cultivation of plant cells based on the plant tissue culture technology. In practicing this new method, it is desired to rapidly grow cultured cells containing a useful substance. Actually, however, cases are known in which no useful substance is produced at all or the amount of products is very small, depending on the composition of the culture medium used. Hence, an improved method is demanded in such cases which will accelerate the production of useful substances.

Furthermore, attention has been attracted to the development of synthetic seeds as a method of cultivating cloned plants in large quantities by the plant tissue culture technology, and practical applications are attempted with various kinds of plants, such as vegetables and rice plants. Synthetic seeds comprise plant regenerating tissues such as adventive buds or embryos embedded and enclosed in a synthetic albumen and a synthetic membrane. The synthetic albumen involves substances that supply the plant regenerating tissue with nutrition and control germination. Calcium alginate is now regarded as the best material for the synthetic membrane, but the use of many other polymeric gelatinizing agents is also being studied. In order to enhance the rate of germination in such a synthetic seed, addition of abscisic acid (a plant hormone) to the synthetic albumem was also reported, but increase in germination rate is not always observed because dissolution and diffusion of this acid in water take a long time. A technique of adding a high-concentration sugar or the like to the synthetic albumen was also proposed, but this promotes the proliferation of unwanted bacteria and inhibits the growth of plants in some cases. Hence, practical applications of synthetic seeds would be further promoted if the growth of plant regenerating tissues such as adventive embryos in the synthetic seeds can be accelerated to enhance the germination rate.

DISCLOSURE OF THE INVENTION

A primary object of this invention is to provide an improved method of plant tissue culture which can effectively proliferate or differentiate plant tissues or cultured cells without using any plant hormone that may inhibit the growth and differentiation of plants.

Another object of this invention is to provide a method of plant tissue culture which can efficiently promote the regeneration of a plant body from plant tissues or cultured cells.

A further object of this invention is to provide a method of plant tissue culture which can grow or proliferate plant cells capable of producing useful substances, thus accelerating the production of these substances.

A further object of this invention is to provide improved synthetic seeds having an enhanced rate of germination.

Thus, according to this invention, there is provided a method of plant tissue culture which comprises culturing a tissue or an organ of a plant, a part of the same or cultured cells in a medium containing a culture filtrate and/or an extract of a photosynthetic procaryotic microorganism.

As preferable examples of the photosynthetic procaryotic microorganism to be used in this invention, there may be mentioned strains of cyanobacteria and photosynthetic bacteria.

According to the method of this invention, it is possible to effectively accelerate the growth of plant tissues, organs and cultured cells, the formation of adventive embryos, the regeneration of a plant body, and the production of useful substances.

This invention also provides a synthetic seed having an enhanced germination rate, which comprises a plant regenerating tissue such as an adventive embryo embedded or enclosed in a synthetic albumen and a synthetic membrane. The synthetic albumen contains therein a culture filtrate and/or an extract of a photosynthetic procaryotic microorganism.

BEST MODE FOR CARRYING OUT THE INVENTION

As examples of the photosynthetic procaryotic microorganism, there may be mentioned strains of cyanobacteria [as classified in R. Rippka and R. Y. Stanier, J. Gen. Microbiol., 111, 1-61 (1979)] and photosynthetic bacteria.

Examples of cyanobacteria include Chlorogloeopisis sp., Dermocarpa sp., Nostoc sp., Synechococcus sp., Oscillatoria sp. and the like. Illustrative examples include Chlorogloeopisis sp. ATCC 27181, Dermocarpa sp. ATCC 29371, Nostoc sp. ATCC 27895, Synechococcus sp. ATCC 27192, ATCC 29404, ATCC 29534 and ATCC 27170, and Oscillatoria sp. ATCC 27906.

Examples of photosynthetic bacteria include Halobacterium sp., Rhodopseudomonas sp., Rhodospirillum sp. and the like. Illustrative examples include *H. cutirubrum* ATCC 33170, *H. mediterranei* ATCC 33500, *H. saccharovorum* ATCC 29252, *H. salinarium* ATCC 19700, *H. sodomense* ATCC 33755, *R. acidophila* ATCC 25092, *R. rutila* ATCC 33872, *R. spheroides* ATCC 17024, *R. viridis* ATCC 19567, *R. blastica* ATCC 33485, *R. molischianum* ATCC 14031, *R. photometricum* ATCC 27871, *R. rubrum* ATCC 277 and ATCC 17031, and *R. tenue* ATCC 25093.

In addition to the above-mentioned microorganisms, as well as variants and mutants thereof, various photosynthetic procaryotic microorganisms isolated from nature, e.g., from salt-water or fresh-water sources can also be used in this invention.

The photosynthetic procaryotic microorganism can be cultured by the use of a medium containing inorganic salts and other nutrients in a tank or outdoors utilizing sunlight to thereby obtain a culture solution. If the microorganism is found abundantly in nature, the saltwater or fresh-water source containing the microorganism may be used as the culture solution.

The culture filtrate of the photosynthetic microorganism may be obtained by filtration or centrifugation of the culture solution obtained by the above-mentioned cultivation method. When the biological activity of the resulting culture filtrate is too low, it may be concentrated under reduced pressure. When the salt concentration in the concentrated culture filtrate becomes too high, it is preferable to use the concentrated culture filtrate after desalting until any adverse effect upon the plant tissues is no longer noticed.

The extract of photosynthetic procaryotic microorganism is obtained by bringing the microbial cells or properly disrupted microbial cells into contact with a suitable solvent at ordinary temperature or at an elevated temperature. A single olvent or a combination of solvents may be used and may be selected depending on the case, but aqueous solvents are preferred in general. Typical examples of such aqueous solvents include water, and aqueous solutions of acids, bases, salts and organic solvents. The microbial cells may be extracted with an organic solvent such as methanol, ethanol, ethyl acetate, ether and the like, followed by removal of the solvent and dissolution of the residue in water. In this invention, there may be used an extract as prepared above, a fraction obtained from the extract, or a properly concentrated or diluted solution obtained from the extract or fraction. In addition, powder obtained by subjecting the extract or fraction to vacuum drying, freeze drying or spray drying may also be used. A fraction of high activity can be obtained from the extract by subjecting it to dialysis, gel filtration, ultrafiltration or other purification process, fractionating the purified product on the basis of molecular weight, and selecting an active fraction.

It has been found that basic substances isolated from the above-mentioned culture filtrate or extract of photosynthetic procaryotic microorganism through fractionation by the use of an organic solvent show particularly high biological activity. This fractionating operation may be carried out on the basis of the theory and method described on pages 25-31 in "Isolation and Purification of Substances" (issued in 1976 from University of Tokyo Press). In the normal procedure of this method, an aqueous solution of a sample is adjusted to pH 3 by addition of an acid, e.g., hydrochloric acid, and then treated with a suitable organic solvent to extract and remove acidic substances. Thereafter, the resulting aqueous layer is adjusted to pH 12 by addition of an alkali, e.g., sodium hydroxide, and a suitable organic solvent is added to extract the basic substances. However, extraction may be carried out at different pH levels and under other conditions. Ethanol, chloroform, ethyl acetate, butanol and the like are frequently used as the solvent, but many other solvents may also be employed. The fraction of basic substances obtained above may also be freed from the solvent, followed by dissolution in water for use.

The effective amount of the culture filtrate and/or the extract of photosynthetic procaryotic microorganism to be added to a basal medium for plant tissue culture may vary with the type of microorganism used, culture conditions, the concentration of extract, and other indefinite factors (such as the changes in the recovery rate of active component and in the volume of solution after the fractionating step), but can be easily determined by experiments. When using, for example, *Synechococcus sp.* ATCC 27192 or *Rhodopseudomonas blastica* ATCC 33485 as the photosynthetic procaryotic microorganism, a culture filtrate concentrated by 100-fold or an extract prepared by extracting 3 g of dried microbial cells with 100 ml of extracting solvent may be added to the basal medium to a concentration in the range from 0.1 to 20%. Higher concentrations may result in lowered effects in some cases.

The basal culture media and cultivation methods commonly employed for conventional plant tissue culture may also be used in this invention. The medium of Murashige and Skoog (1962)(hereinafter abbreviated as "MS medium") may be mentioned as a typical basal medium, but many other media suited for plant culture and modifications thereof may also be used case by case. In addition to the culture filtrate or the extract of photosynthetic procaryotic microorganism, plant hormones, coconut milk, casein decomposition products and yeast extract employed in ordinary cultivation may also be added to the medium as required.

The method of this invention can be applied to any kinds of plants that have totipotency and allow tissue culture. Tissues, organs, part of the same or cultured cells of these plants may be subjected to cultivation, and those subjected to primary culture or passage culture may also be used in this invention.

The following examples will further illustrate the invention. In the examples, the description "%" means "% by w/v".

Preparation of carrot cultured cells, cultivation of its adventive embryos, and preparation of the culture filtrate and the extract of photosynthetic procaryotic microorganism were carried out as described below.

(I) Preparation of Carrot Cultured Cells and Cultivation of Its Adventive Embryos Hypocotyls grown from carrot (*Daucus carota* L. cv. Kurodagosun) sterile seeds to a length of about 10 cm were cut into pieces about 1 cm long, and these pieces were cultured in a modified MS medium (MS medium with 3% sucrose and 1 mg/l 2,4-D (2,4-dichlorophenoxyacetic acid which is a kind of auxin) added thereto; pH: 5.5 to 5.7) at 25° C. under dark conditions. After cultivation for about one month, the cultured tissues were transplanted to a new medium containing 2,4-D at reduced concentration of 0.11 mg/l, and subjected to shaking culture using a reciprocating shaker moving back and forth 90 times per minute. Thereafter, transplantation to a new medium containing 0.11 mg/l 2,4-D was repeated at one week intervals to prepare carrot cultured cells.

It is known that carrot cultured cells are capable of forming adventive embryos through morphological differentiation. Hence, the cultured cells obtained above were cultured in MS medium (basal medium containing no 2,4-D) to prepare adventive embryos.

(II) Preparation of Culture Filtrate and Extract of Photosynthetic Procaryotic Microorganism

*Synechococcus sp.* ATCC 27192 was used as a strain of cyanobacteria, and *Rhodopseudomonas blastica* ATCC 33485 was used as a strain of photosynthetic microorganisms. Each of these two strains was cultured under conditions specified by the American Type Culture Collection, the resulting culture solution was subjected to centrifugal filtration, and the filtrate was concentrated 100-fold by using an evaporator. The concentrate was then desalted in a desalter of mosaic charged membrane type (Desaltion DS-103; Tosoh Co., Ltd.), followed by filtration through a 0.45 μm membrane filter, and the filtrate thus obtained was used as a culture filtrate of photosynthetic procaryotic microorganism. Separately, microbial cells were collected from the culture solution obtained above, freeze-dried and suspended in water to a concentration of 3%. This suspension was heated at 100° C. for 60 minutes to effect extraction and then centrifuged.

The resulting supernatant was filtered through 0.45 μm membrane filter, and the filtrate thus obtained was used as an extract of photosynthetic procaryotic microorganism.

EXAMPLE 1

Proliferation of Carrot Cultured Cells

The carrot cultured cells prepared in (I) above were subjected to shaking culture at 25° C. under dark conditions for 12 days in MS medium containing 3% sucrose and 0.11 mg/l 2,4-D and in a modified medium thereof (further containing 1% of the extract of photosynthetic procaryotic microorganism prepared in (II) above), and the number of grown cells was measured. The result is shown in Table 1.

TABLE 1

| Additive | Number of cells per ml[*1] | |
|---|---|---|
| | on 6th day | on 12th day |
| None | $4.0 \times 10^6$ | $5.2 \times 10^6$ |
| Cyanobacteria | $5.5 \times 10^6$ | $7.3 \times 10^6$ |
| Photosynthetic bacteria | $5.3 \times 10^6$ | $7.1 \times 10^6$ |

Note) [*1] The number of cells was measured as described below according to the method described on page 38 in "Technology of Plant Tissue Culture" (1983; Takeuchi, Nakajima and Furuya; Asakura-shoten).

Shaking was continued at 30° C. for 60 minutes (amplitude: 7 cm . reciprocating frequency: 90 per minute) using 2% cellulase Onozuka R-10, 1% Macerozyme R-10, 2% Driselase, 0.5% $CaCl_2 \cdot 2H_2O$ and 0.7M mannitol, followed by shaking at a reciprocating frequency of 50 per minute for 90 minutes, and the number of released protoplasts was measured by using a hemocytometer of 0.1 mm depth.

EXAMPLE 2

Regeneration of Plant Body from Carrot Cultured Cells

The carrot cultured cells prepared in (I) above were subjected to shaking culture at 25° C. under dark conditions for 30 days in MS medium containing 3% sucrose and in a modified medium thereof (further containing 1% of the culture filtrate or the extract of photosynthetic procaryotic microorganism prepared in (II) above), and the resulting adventive embryos were observed on the 10th, 20th and 30th days. The result is shown in Table 2.

TABLE 2

| Additive | Rate of forming adventive embryos (%)[*2] | | Budding and rooting conditions[*3] |
|---|---|---|---|
| | Culture period (days) | | |
| | on 10th day | on 20th day | on 30th day |
| None | 5 | 38 | X |

TABLE 2-continued

| Additive | Rate of forming adventive embryos (%)*2 | | Budding and rooting conditions*3 |
|---|---|---|---|
| | Culture period (days) | | |
| | on 10th day | on 20th day | on 30th day |
| Cyanobacteria | | | |
| culture filtrate | 8 | 49 | ○ |
| extract | 10 | 63 | ○ |
| Photosynthetic bacteria | | | |
| culture filtrate | 7 | 51 | ○ |
| extract | 8 | 59 | ○ |

Note)
*2Rate of forming adventive embryos: the number of adventive embryos divided by the number of total cells or cell aggregates
*3Explanation of symbols:
○: Morphological changes of adventive embryos (budding and rooting) and growth were both rapid.
X: No rapid morphological change of adventive embryos was observed.

EXAMPLE 3

Regeneration of Plant Body from Carrot Adventive Embryos

Adventive embryos prepared in (I) above were selected by using 148 μm and 200 μm Nylon meshes, and the samples of 148 to 200 μm in size thus selected (globular to torpedo-shaped embryos) were used in this example. These adventive embryos were subjected to shaking culture at 25° C. under bright conditions (2000 lux × 16 hours) over a period of 30 days in MS medium containing no plant hormone and in a modified medium thereof (containing 1.5% of the culture filtrate or the extract of photosynthetic procaryotic microorganism prepared in (II) above), and the conditions of the resulting adventive embryos were observed. The result is shown in Table 3(1).

TABLE 3(1)

| Additive | Conditions of adventive embryos (cultured for 30 days) |
|---|---|
| None | X |
| Cyanobacteria | |
| culture filtrate | Δ |
| extract | ○ |
| Photosynthetic bacteria | |
| culture filtrate | Δ |
| extract | ○ |

Note)
*4Explanation of symbols
X: Growth of embryos was scarcely observed.
Δ: No regeneration of plant body was observed within the above period, although growth of embryos was observed.
○: Regeneration of plant body through mature embryos was observed.

In addition, the effects of high-molecular and low-molecular fractions involved in the culture filtrate and the extract of photosynthetic procaryotic microorganism upon regeneration of plant body were examined as described below. The culture filtrate and the extract of photosynthetic procaryotic microorganism prepared in (II) above (50 ml each) were dialyzed against one liter of distilled water through a cellulose tube for dialysis ("Cellulose Tube 30/32" of VISKASE Inc.), and the dialyzate thus obtained was used as the high-molecular fraction, while the external solution (the solution diffused outwardly through the cellulose tube) was concentrated under reduced pressure to 50 ml, and the concentrate thus obtained was used as the low-molecular fraction. On the other hand, the adventive embryos prepared in (I) above were selected by using 425 μm and 800 μm Nylon meshes. The samples of 425 to 800 μm in size thus obtained were subjected to shaking culture at 25° C. under bright conditions (2000 lux × 16 hours) over a period of ten days in MS medium containing no plant hormone and in a modified medium thereof containing 200 μg/ml of the high-molecular or low-molecular fraction involved in the culture filtrate or the extract of photosynthetic procaryotic microorganism, and the conditions of regeneration of the plant body were observed. The result is shown in Table 3(2).

TABLE 3(2)

| Additive | Total number of embryos | Immature plant Number | Immature plant Rate (%) | Mature plant Number | Mature plant Rate (%) |
|---|---|---|---|---|---|
| None | 430 | 13 | 3 | 0 | 0 |
| Cyanobacteria Extract | | | | | |
| High-molecular Fraction | 410 | 107 | 26 | 57 | 14 |
| Low-molecular fraction | 470 | 38 | 8 | 15 | 3 |
| Culture filtrate | | | | | |
| High-molecular fraction | 415 | 42 | 10 | 29 | 7 |
| Lo-molecular fraction | 432 | 22 | 5 | 9 | 2 |
| Photosynthetic bacteria Extract | | | | | |
| High-molecular fraction | 428 | 72 | 17 | 38 | 9 |
| Low-molecular fraction | 443 | 31 | 7 | 18 | 4 |
| Culture filtrate | | | | | |
| High-molecular fraction | 420 | 34 | 8 | 17 | 4 |
| Low-molecular fraction | 442 | 13 | 3 | 9 | 2 |

EXAMPLE 4

Regeneration of Plant Body from Cattleya Protocorm-Like Bodies

The starting material used in this example is protocorm-like bodies (hereinafter abbreviated as PLBs) derived from the meristematic tissue close to the growing point of lateral buds of Laeliocattleya, and a medium containing Hyponex (6.5-6-19), 7% potato juice and 2% sucrose as carbon source was used for cultivation of PLBs.

Mature PLBs were selected after the early culture thereof, and each of the selected PLBs was cut into four pieces, thus preparing PLB samples.

These PLB samples were cultured at 25° C. under bright conditions (2000 lux × 16 hours) over a period of 60 days on an agar medium containing the medium for cultivation of PLBs and on a modified agar medium thereof (further containing 0.5% of the culture filtrate or the extract of photosynthetic procaryotic microorganism prepared in (II) above). The conditions of PLBs on these agar media were observed after 40 days, and the number of grown PLBs and the number of shoots put forth therefrom were observed after 60 days. The result is shown in Table 4.

TABLE 4

| Additive | Conditions after 40 days (per 50 applied PLBs) | | Total PLBs (after 60 days) | |
|---|---|---|---|---|
| | Number of dead PLBs | Number of grown PLBs | Total number of PLBs | Number of PLBs having shoots |
| None | 14 | 36 | 163 | 41 |
| Cyanobacteria | | | | |
| culture filtrate | 8 | 42 | 213 | 89 |
| extract | 4 | 46 | 254 | 101 |
| Photosynthetic bacteria | | | | |
| culture filtrate | 9 | 41 | 207 | 72 |
| extract | 5 | 45 | 243 | 98 |

EXAMPLE 5

Regeneration of Plant Body from Tobacco Calluses

The starting material used in this example is calluses derived from the cauline pith tissues of *Nicotiana tabacum* L. cv. Bright Yellow. The calluses were subjected to passage culture on an agar medium of MS medium containing 1 mg/l indoleacetic acid and 0.1mg/l kinetin.

A plurality of test tubes were prepared, each of which received therein the same agar medium as used in the passage culture or a modified agar medium thereof (further containing 1.5% of the culture filtrate or the extract of photosynthetic procaryotic microorganism prepared in (II) above). Twenty-five (25) test tubes were prepared per each kind of media. The calluses subjected to the passage culture were cut into pieces of 5 mm square by using a razor. Each cut piece was put on the agar medium in the respective test tubes and cultured at 25° C. under bright conditions (2000 lux×16 hours) over a period of 14 days. The formation of shoots was then observed. The result is shown in Table 5.

TABLE 5

| Additive | Number of applied calluses | Number of formed shoots |
|---|---|---|
| None | 25 | 75 |
| Cyanobacteria | | |
| culture filtrate | 25 | 91 |
| extract | 25 | 100 |
| Photosynthetic bacteria | | |
| culture filtrate | 25 | 98 |
| extract | 25 | 105 |

EXAMPLE 6

Regeneration of Plant Body from African Violet (*Saintpaulia ionatha*) Petioles

MS medium containing 1 mg/l naphthaleneacetic acid and 1 mg/l kinetin and a modified medium thereof (further containing 2.0% of the extract of photosynthetic procaryotic microorganism prepared in (II) above) were prepared. Saintpaulia petioles were cut into pieces about 5 mm long. Each cut piece was put on an agar medium of each of the above media placed in a 300 ml conical flask, and cultured under dark conditions for one week and then at 20° C. for 30 days under bright conditions (2000 lux×16 hours), and the conditions of formed shoots and leaves were observed. The result is shown in Table 6.

TABLE 6

| Additive | Conditions of shoot formation | |
|---|---|---|
| | Number of leaves | Average size (cm) (leaf + petiole) |
| None | 18 | 1.7 |

TABLE 6-continued

| Additive | Conditions of shoot formation | |
|---|---|---|
| | Number of leaves | Average size (cm) (leaf + petiole) |
| Cyanobacteria | 25 | 2.3 |
| Photosynthetic bacteria | 24 | 2.6 |

EXAMPLE 7

Production of Carotenoid from Carrot Cultured Cells

Cells capable of producing carotenoid derived from the roots of carrot (*Daucus carota* L. cv. Kintoki) were used as the starting material in this example.

MS medium containing 3% sucrose, 1 mg/l 2,4-D and 1% agar (pH 5.5 to 5.7) and a modified medium thereof (further containing 1% of the culture filtrate or the extract of photosynthetic procaryotic microorganism) were prepared. The cells were cultured on each of the above media at 25° C. for 50 days under dark conditions, and the amount of carotenoid accumulated in the cells was measured.

The amount of carotenoid was determined by measuring the wet weight of cultured cells, disrupting the cells in a mortar, extracting the disrupted cells with a small volume of acetone, adding 3 ml petroleum ether to the extract to transfer the carotenoid from the acetone to petroleum ether layer, and measuring the absorbance of the ether layer at 453 nm with a spectrophotometer. The result is shown in Table 7.

TABLE 7

| Additive | Wet weight (g) | Amt. of carotenoid (μg/g-wet weight) |
|---|---|---|
| None | 4.2 | 22 |
| Cyanobacteria | | |
| culture filtrate | 5.6 | 52 |
| extract | 6.9 | 48 |
| Photosynthetic bacteria | | |
| culture filtrate | 5.1 | 43 |
| extract | 6.2 | 40 |

EXAMPLE 8

Production of Betacyanin from Cultured Cells of Pokeweed(*Phytolacca americana*)

Cells capable of producing betacyanin derived from the stems of *Phytolacca americana* were used as the starting material in this example.

MS medium containing 3% sucrose and 0.1 mg/l 2,4-D (pH 5.5 to 5.7) and a modified medium thereof (further containing 1% of the culture filtrate or the extract of photosynthetic procaryotic microorganism prepared in (II) above) were prepared. The cells were subjected to liquid suspension culture in each of the above media at 25° C. for 14 days under bright conditions (2000 lux), and the amount of betacyanin accumulated in the cells was measured.

The amount of betacyanin was determined by measuring the wet weight of cultured cells, disrupting the cells in a mortar, extracting the disrupted cells with a small volume of water, centrifuging the resulting mixture, and measuring the absorbance of the supernatant at 535 nm with a spectrophotometer. The result is shown in Table 8.

TABLE 8

| Additive | Wet weight (g) | Amt. of betacyanin (μg/g-wet weight) |
|---|---|---|
| None | 4.2 | 149 |
| Cyanobacteria | | |
| culture filtrate | 19.8 | 258 |
| extract | 14.6 | 225 |
| Photosynthetic bacteria | | |
| culture filtrate | 16.3 | 232 |
| extract | 14.8 | 248 |

EXAMPLE 9

Growth of Carrot Adventive Embryos

The basic substances contained in the culture filtrate and the extract of photosynthetic procaryotic microorganism were fractionated as described below. 1N-HCl was added to each of the culture filtrate and the extract of photosynthetic procaryotic microorganism prepared in (II) above to adjust the pH to 3, chloroform was then added to extract and remove acidic substances involved. Thereafter, the resulting aqueous layer was adjusted to pH 12 by addition of 1N-NaOH, and chloroform was added to extract the basic substances. Chloroform was distilled off under reduced pressure from the extract, the residue was dissolved in ultrapure water of pH 4, and the solution was freeze-dried to obtain a sample of basic substances.

On the other hand, carrot adventive embryos prepared in (I) above were screened through a 148 μm Nylon mesh, and those grown to a size of 148 μm or more were collected. Most of the collected embryos were of globular to heart shape.

These adventive embryos were cultured in MS medium containing no plant hormone; in a modified medium thereof containing 1.5% of the culture filtrate or the extract of photosynthetic procaryotic microorganism; and in another modified medium thereof containing 100 ppm of the basic substances isolated from the culture filtrate or the extract; at 25° C. under bright conditions (2000 lux×12 hours) over a period of one month, and the growth conditions of the embryos were examined. The result is shown in Table 9.

TABLE 9

| Additive | Number of grown adventive embryos[5] (per ml) |
|---|---|
| None | 60 (20)[6] |
| Cyanobacteria | |
| culture filtrate | 200 (120) |
| extract | 180 (160) |
| basic substances in culture filtrate | 420 (310) |
| basic substances in extract | 680 (530) |
| Photosynthetic bacteria | |
| culture filtrate | 250 (180) |
| extract | 310 (210) |
| basic substances | 480 (200) |

TABLE 9-continued

| Additive | Number of grown adventive embryos[5] (per ml) |
|---|---|
| in culture filtrate | |
| basic substances in extract | 530 (310) |

Note)
[5]Grown adventive embryos are those grown to a length of at least 5 mm.
[6]Values in ( ) are the number of adventive embryos having regenerated buds and roots.

EXAMPLE 10

Preparation of Synthetic Seeds Using Carrot Adventive Embryos

The extract of photosynthetic procaryotic microorganism prepared in (II) above (50 ml) was dialyzed against one liter of distilled water through a cellulose tube for dialysis ("Cellulose Tube 30/32" of VISKASE Inc.), and the dialyzate thus obtained was used as the high-molecular fraction, while the external solution was concentrated under reduced pressure to 50 ml, and the concentrate thus obtained was used as the low-molecular fraction.

On the other hand, carrot adventive embryos prepared in (I) above were screened through a 148 μm Nylon mesh, and those grown to a size of 148 μm or more were collected. Most of the collected embryos were of globular to heart shape.

These adventive embryos were suspended in 25 ml of MS medium, this suspension was mixed with 75 ml of MS medium containing 3% sodium alginate as embedding agent. Into the resulting 100 ml of the mixed solution was added the culture filtrate or the extract of photosynthetic procaryotic microorganism prepared in (II) above, or the high-molecular or the low-molecular fraction obtained above to a concentration of 10%. The mixed solution thus prepared was added dropwise into a 50 mM $CaCl_2$ solution to obtain globular synthetic seeds having a synthetic membrane made of calcium alginate.

These synthetic seeds were cultured in a sterile manner at 25° C. under bright conditions (2000 lux×12 hours) over a period of one month, and the conditions of budding and rooting were observed. The result is shown in Table 10.

TABLE 10

| Additive | Number of synthetic seeds | Number of roots | Number of buds |
|---|---|---|---|
| None | 101 | 23 | 21 |
| Cyanobacteria | | | |
| culture filtrate | 128 | 48 | 39 |
| extract | 130 | 68 | 72 |
| high-molecular fraction in extract | 138 | 113 | 89 |
| low-molecular fraction in extract | 121 | 43 | 38 |
| Photosynthetic bacteria | | | |
| culture filtrate | 128 | 54 | 38 |
| extract | 130 | 78 | 60 |
| high-molecular fraction in extract | 134 | 101 | 73 |
| low-molecular fraction in extract | 131 | 64 | 51 |

We claim:

1. A synthetic seed comprising a plant regenerating tissue embedded and enclosed in a synthetic albumen and a synthetic membrane, characterized in that said synthetic albumen contains one or more members selected from the group consisting of a culture filtrate from a photosynthetic procaryotic microorganism, an extract from said microorganism, a high molecular weight fraction dialyzed from said culture filtrate, a high molecular weight fraction dialyzed from said extract, a low molecular weight fraction dialyzed from said culture filtrate and a low molecular weight fraction dialyzed from said extract, wherein said plant regenerating tissue is not an intact seed.

2. The synthetic seed as defined in claim 1, wherein said photosynthetic procaryotic microorganism is a strain of cyanobacteria.

3. The synthetic seed as defined in claim 2, wherein said cyanobacteria is synechococcus.

4. The synthetic seed as defined in claim 1, wherein said photosynthetic procaryotic microorganism is a strain of photosynthetic bacteria.

5. The synthetic seed as defined in claim 4, wherein said photosynthetic bacteria is Rhodopseudomonas.

6. A synthetic seed comprising a plant regenerating tissue embedded and enclosed in a synthetic albumen and a synthetic membrane, characterized in that said synthetic albumen contains a culture filtrate from a photosynthetic procaryotic microorganism, wherein said plant regenerating tissue is not an intact seed.

7. The synthetic seed as defined in claim 6, wherein said photosynthetic procaryotic microorganism is a strain of cyanobacteria.

8. The synthetic seed as defined in claim 7, wherein said cyanobacteria is Synechococcus.

9. The synthetic seed as defined in claim 6, wherein said photosynthetic procaryotic microorganism is a strain of photosynthetic bacteria.

10. The synthetic seed as defined in claim 9, wherein said photosynthetic bacteria is Rhodopseudomonas.

11. A synthetic seed comprising a plant regenerating tissue embedded and enclosed in a synthetic albumen and a synthetic membrane, characterized in that said synthetic albumen contains an extract from a photosynthetic procaryotic microorganism, wherein said plant regenerating tissue is not an intact seed.

12. The synthetic seed as defined in claim 11, wherein said photosynthetic procaryotic microorganism is a strain of cyanobacteria.

13. The synthetic seed as defined in claim 12, wherein said cyanobacteria is Synechococcus.

14. The synthetic seed as defined in claim 11, wherein said photosynthetic procaryotic microorganism is a strain of photosynthetic bacteria.

15. The synthetic seed as defined in claim 14, wherein said photosynthetic bacteria is Rhodopseudomonas.

* * * * *